United States Patent [19]
Bone et al.

[11] Patent Number: 5,612,369
[45] Date of Patent: Mar. 18, 1997

[54] THROMBIN INHIBITORS

[75] Inventors: Roger F. Bone, Bridgewater; Richard M. Soll, Lawrenceville, both of N.J.; Carl L. Illig, Phoenixville, Pa.; Tianbao Lu, Exton, Pa.; Nalin L. Subasinghe, West Chester, Pa.

[73] Assignee: 3-Dimensional Pharmaceuticals, Inc., Exton, Pa.

[21] Appl. No.: 487,421

[22] Filed: Jun. 7, 1995

[51] Int. Cl.$^6$ .......................... A61K 31/40; C07D 207/08
[52] U.S. Cl. ............................................ 514/423; 548/537
[58] Field of Search .............................. 548/537; 514/423

[56] References Cited

U.S. PATENT DOCUMENTS 5,248,673  9/1993  Balasubramanian et al. .......... 514/212

FOREIGN PATENT DOCUMENTS

WO93/15756  8/1993  WIPO .
WO94/20526  9/1994  WIPO .
WO95/23609  9/1995  WIPO .

OTHER PUBLICATIONS

Bajusz S., Interaction of Trypsin–like Enzymes with Small Inhibitors, *Symp. Biol. Hung.* 25:277–298 (1984).
Church and Hoffman, Heparin Cofactor II and Thrombin, *Trends in Cardiovascular Medicine* 4(3):140–146 (1993).
Claeson G., Synthetic peptides and peptidomimetics as substrates and inhibitors of thrombin and other proteases in the blood coagulation system, *Blood Coagulation and Fibrinolysis* 5:411–436 (Jun. 1994).
Coughlin S.R., Molecular Mechanisms of Thrombin Signaling, *Seminars in Hematology* 31(4):270–277 (Oct. 1994).
Harker L.A., Strategies for inhibiting the effects of thrombin, *Blood Coagulation and Fibrinolysis* 5 (Suppl 1):S47–S58 (Jan. 1994).
Lefkovits and Topol, Direct Thrombin Inhibitors in Cardiovascular Medicine, *Circulation* 90(3):1522–1536 (Sep. 1994).
Nelson et al., Opioid Peptides:Analysis of Specificity and Multiple Binding Modes Through Computer–Aided Drug design and Structure Activity Studies, *NIDA Res. Monogr.* 69:204–230 (1986).
Raj et al., Long–term Oral Anticoagulant Therapy:Update on Indicators, Therapeutic Ranges, and Monitoring, *The American Journal of the Medical Sciences* 307(2):128–32 (Feb. 1994).
Tapparelli et al., Synthetic low–molecular weight thrombin inhibitors:molecular design and pharmacological profile, *Trends in Pharmacological Sciences* 14:366–376 (1993).
Weitz and Hirsh, New Anticoagulant Strategies, *Journal of Laboratory Clinical Medicine* 122(4):364–373 (1993).

*Primary Examiner*—Patricia L. Morris
*Attorney, Agent, or Firm*—Sterne, Kessler, Goldstein, Fox P.L.L.C.

[57] ABSTRACT

The present invention is directed to novel compounds that are thrombin inhibitors and are useful for the treatment of arterial and venous thrombotic occlusive disorders, inflammation, cancer, and neurodegenerative diseases. The compounds have the general Formula I:

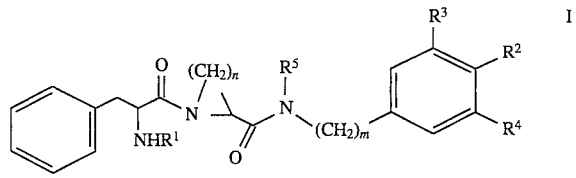

and pharmaceutically acceptable salts thereof; wherein $R^1$, $R^2$, $R^3$, $R^4$, $R^5$, n and m are defined herein.

14 Claims, No Drawings

THROMBIN INHIBITORS

FIELD OF THE INVENTION

The present invention relates to novel compounds that are inhibitors of thrombin activity, their pharmaceutically acceptable salts, and pharmaceutical compositions thereof. The compounds are useful in the treatment of arterial and venous thrombotic occlusive disorders, inflammation, cancer and neurodegenerative disease.

BACKGROUND OF THE INVENTION

The serine protease thrombin occupies a central role in hemostasis and thrombosis (Tapparelli et al., *Trends in Pharmacological Sciences* 14:366–376 (1993); Lefkovits and Topol, *Circulation* 90(3):1522–1536 (1994); Harker, *Blood Coagulation and Fibrinolysis* 5 (Suppl 1):S47–S58 (1994)). Activation of the coagulation cascade through either the intrinsic pathway (contact activation) or the extrinsic pathway (activation by exposure of plasma to a non-endothelial surface, damage to vessel walls or tissue factor release) leads to a series of biochemical events that converge on thrombin. Thrombin cleaves fibrinogen ultimately leading to a hemostatic plug (clot formation), potently activates platelets through a unique proteolytic cleavage of the cell surface thrombin receptor (Coughlin, *Seminars in Hematology* 31(4):270–277 (1994)), and autoamplifies its own production through a feedback mechanism.

As a multifactorial protein, thrombin induces a number of effects on platelets, endothelial cells, smooth muscle cells, leukocytes, the heart, and neurons (Tapparelli et al., Trends in Pharmacological Sciences 14:366–376 (1993); Church and Hoffman, *Trends in Cardiovascular Medicine* 4(3): 140–146 (1993)). Platelet activation leads to shape change and aggregation as well as the synthesis, release and secretion of vasoactive substances and lysosomal enzymes. Endothelial cell activation results in the secretion of stimulatory agents leading to increased vascular permeability and adhesiveness for mononuclear cells, one consequence of which is extravasation of leukocytes at the site of thrombin generation. Thrombin induces fibroblast and smooth muscle cell proliferation suggesting that thrombin plays a key role in lesion development following vascular damage. Enhanced automaticity and prolongation of repolarization have been observed in cardiac myocytes showing sensitivity to thrombin. Normal neuronal development has been shown also to be influenced by thrombin. Thus, inhibitors of thrombin function have therapeutic potential in a host of cardiovascular and non-cardiovascular diseases, including: myocardial infarction; unstable angina; stroke; restenosis; deep vein thrombosis; disseminated intravascular coagulation caused by trauma, sepsis or tumor metastasis; hemodialysis; cardiopulmonary bypass surgery; adult respiratory distress syndrome; endotoxic shock; rheumatoid arthritis; ulcerative colitis; induration; metastasis; hypercoaguability during chemotherapy; Alzheimer's disease; and Down's syndrome.

To date only three classes of compounds (heparins, low-molecular weight heparins and coumarins, such as warfarin) have been used in anticoagulant therapy. Each class has severe limitations and liabilities (Weitz and Hirsh, *Journal of Laboratory Clinical Medicine* 122:364–373 (1993); Raj et al., *The American Journal of the Medical Sciences* 307(2):128 (1994)). All three classes indirectly inhibit thrombin. Heparin and low-molecular weight heparins augment antithrombin III and/or heparin cofactor II inhibition of thrombin, whereas coumarins inhibit vitamin K-dependent post-translational modification. Close monitoring and titration of therapeutic doses is required when employing these agents due to patient variability. Hemorrhagic complications due to bleeding are an encountered side effect. In fact, bleeding remains as the most common side effect of long term oral anticoagulant therapy. Lack of activity in arterial thrombosis in the case of heparin is due to its inability to inhibit clot bound thrombin. Lack of oral activity in the case of heparins and low-molecular weight heparins preclude their use for chronic administration.

Direct thrombin inhibitors of various structural classes have been identified recently (Tapparelli et al., *Trends in Pharmacological Sciences* 14:366–376 (1993); Claeson, *Blood Coagulation and Fibrinolysis* 5:411–436 (1994); Lefkovits and Topol, *Circulation* 90(3):1522–1536 (1994)). Representative compounds that act by inhibiting the active site of thrombin include the α-chloroketone D-phenylalanyl-L-prolyl-L-arginyl chloromethylketone (PPACK), the boro-arginine DUP714, the peptide arginal GYK114766, the cyclic peptides cyclotheonamides A and B, the benzamidine NAPAP, and the arylsulphonylarginine argatroban. The thrombin inhibitory peptides hirudin and hirulogs additionally span through the active and exosite domains of thrombin. The peptide hirugen and single-stranded DNA aptamers inhibit thrombin through exosite occupancy.

Experimental studies with direct thrombin inhibitors have shown efficacious antithrombotic effects in various animal models (Lefkovits and Topol, *Circulation* 90(3):1522–1536 (1994)). Direct thrombin inhibitors may take on an important adjunctive role in thrombolysis and may offer a beneficial role in the field of coronary intervention. Clinical studies with direct thrombin inhibitors for treating acute myocardial infarction, for treating unstable angina, and for patients undergoing diagnostic coronary angiography have provided encouraging results. Nevertheless, these classes of antithrombotic agents still suffer from one or more of the following liabilities: (1) poor oral bioavailability due to the peptidic or oligonucleotidic nature of these agents, or high molecular weight or charged nature of the agents; (2) potential for bleeding complications; (3) poor selectivity towards thrombin versus other serine proteases (which may lead to severe and sometimes fatal hypotension and respiratory depression in animal models); (4) liver toxicity; or (5) cost effectiveness.

A need continues to exist for non-peptidic compounds that are potent and selective inhibitors of thrombin, and which possess greater bioavailability and fewer side-effects than currently available direct inhibitors of thrombin.

U.S. Pat. No. 5,248,673, issued Sep. 28, 1993, discloses bisamidine derivatives as thrombin inhibitors. The patent discloses that these compounds can be used in the treatment of thrombosis, ischemia and stroke.

PCT Published Application WO 93/15756, published Aug. 19, 1993, discloses peptide aldehyde analogs that exhibit thrombin inhibiting activity.

PCT Published Application WO 94/20526, published Sep. 15, 1994, discloses peptide derivatives having a C-terminal boronic acid group. The published application discloses that these protease inhibitory activity.

Nelson et al., *NIDA Res. Monogr.* 69:204–230 (1986) discloses analogs of morphiceptin, an opioid peptide and the testing thereof as μ-receptor agonists and antagonists. The peptide analog L-tyrosyl-N-[2-(4-nitrophenyl)ethyl]-L-prolinamide is disclosed.

Bajusz, *Symp. Biol. Hung.* 25:277–298 (1984) reviews the structural and inhibitory properties of peptide inhibitors of trypsin-like enzymes, such as thrombin, plasmin, kallikrein and trypsin. The compound D-phenylalanyl-N-[2-[4-[(aminoiminomethyl)amino]phenyl]ethyl-L-prolinamide is disclosed.

SUMMARY OF THE INVENTION

The present invention is directed to novel having Formula I (below). Also provided is a process for preparing compounds of Formula I. The novel compounds of the present invention exhibit antithrombotic activity via direct inhibition of thrombin, or are intermediates useful for forming compounds having antithrombotic activity. Also provided is a method of treating thrombosis, ischemia, stroke, restenosis or inflammation in a mammal in need of such treatment comprising administering to said mammal an effective amount of a compound of Formula I. Further provided is a pharmaceutical composition comprising a compound of Formula I and one or more pharmaceutically acceptable carriers or diluents.

DETAILED DESCRIPTION OF THE PREFERRED EMBODIMENTS

The present invention is directed to compounds of Formula I:

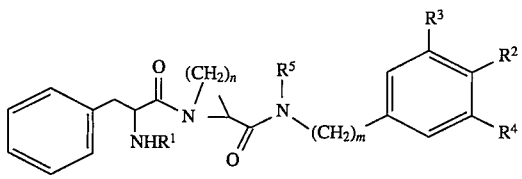

and pharmaceutically acceptable salts thereof;
wherein
$R^1$ is one of hydrogen, $-SO_2R^8$, $-CONHR^8$ or $-CO_2R^8$, where $R^8$ is one of hydrogen, alkyl, alkenyl, alkynyl, aryl or arylalkyl;

$R^2$ is one of hydroxy or $-NR^6R^7$;

$R^3$ and $R^4$ are independently one of hydrogen, hydroxy, $-NR^6R^7$, alkyl, aryl, arylalkyl, alkoxy, halogen, haloalkyl, aminoalkyl or hydroxyalkyl;

$R^5$, $R^6$ and $R^7$ are independently one of hydrogen, alkyl, aryl or arylalkyl;

n is from 2 to 6; and
m is from 1 to 6.

Preferred compounds of the present invention are those of Formula I wherein $R^1$ is one of hydrogen or $-CO_2-R^8$, wherein $R^8$ is defined as above, and is preferably benzyl; $R^2$ is hydroxy or $-NR^6R^7$, wherein $R^6$ and $R^7$ are defined as above, and are preferably independently hydrogen or $C_{1-6}$alkyl; $R^3$ and $R^4$ are independently one of hydrogen, hydroxy, $C_{1-6}$alkyl or $C_{1-6}$alkoxy; $R^5$ is hydrogen; n is from 2 to 6, more preferably 2 to 5, even more preferably 2, 3 or 4, and most preferably 3; and m is from 1 to 6, preferably 1 to 4, and most preferably 1 or 2.

More preferred are compounds of Formula I wherein $R^1$ is one of hydrogen or $-CO_2-$benzyl; $R^2$ is hydroxy, $-NH_2$ or $-N(CH_3)_2$; $R^3$ and $R^4$ are independently one of hydrogen, hydroxy or methoxy; $R^5$ is hydrogen; n is 3; and m is 1 or 2.

The most preferred compounds include: N-CBZ-D-phenylalanyl- N-[2-(4-hydroxy-3-methoxybenzyl)]-L-prolinamide, D-phenylalanyl- N-[2-(4-hydroxy-3-methoxybenzyl)]- L-prolinamide, N-CBZ-D-phenylalanyl-N-[2-(4-dimethylaminobenzyl)]-L-prolinamide, D-phenylalanyl-N-[2-(4-dimethylaminobenzyl)]-L-prolinamide, N-CBZ-D-phenylalanyl-N-[2-(3,4-dihydroxyphenethyl)]-L-prolinamide, N-CBZ-D-phenylalanyl-N-[2-(4-hydroxyphenethyl)]-L-prolinamide, N-CBZ-D-phenylalanyl-N-[2-(4-aminobenzyl)]-L-prolinamide, D-phenylalanyl-N-[2-(4-aminobenzyl)]-L-prolinamide, N-CBZ-D-phenylalanyl-N-[2-(4-aminophenethyl)]-L-prolinamide, N-CBZ-D-phenylalanyl-N-[2-(3,5-dimethoxy-4-hydroxyphenethyl)]- L-prolinamide, and N-CBZ-D-phenylalanyl-N-[2-(3-methoxy-4-hydroxyphenethyl)]- L-prolinamide.

It is also to be understood that the present invention is considered to include stereoisomers as well as optical isomers, e.g. mixtures of enantiomers as well as individual enantiomers and diastereomers, which arise as a consequence of structural asymmetry in selected compounds of the present series.

For medicinal use, the pharmaceutically acceptable acid addition salts, those salts in which the anion does not contribute significantly to toxicity or pharmacological activity of the organic cation, are preferred. The acid addition salts are obtained either by reaction of an organic base of Formula I with an organic or inorganic acid, preferably by contact in solution, or by any of the standard methods detailed in the literature available to any practitioner skilled in the art. Examples of useful organic acids are carboxylic acids such as maleic acid, acetic acid, tartaric acid, propionic acid, fumaric acid, isethionic acid, succinic acid, pamoic acid, cyclamic acid, pivalic acid and the like; useful inorganic acids are hydrohalide acids such as HCl, HBr, HI; sulfuric acid; phosphoric acid and the like.

The term "alkyl" as employed herein includes both straight and branched chain radicals of up to 12 carbons, preferably 1–8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl and the various branched chain isomers thereof.

The term "aryl" as employed herein by itself or as part of another group refers to monocyclic or bicyclic aromatic groups containing from 6 to 12 carbons in the ring portion, preferably 6–10 carbons in the ring portion, such as phenyl, naphthyl or tetrahydronaphthyl.

The term "aralkyl" or "arylalkyl" as used herein by itself or as part of another group refers to $C_{1-6}$alkyl groups as discussed above having an aryl substituent, such as benzyl, phenethyl or 2-naphthylmethyl.

The terms "alkoxy," or "aralkoxy" includes any of the above alkyl or aralkyl groups linked to an oxygen atom.

The term "halogen" or "halo" as used herein by itself or as part of another group refers to chlorine, bromine, fluorine or iodine with chlorine being preferred.

The term "alkenyl" by itself or as part of another group as employed herein includes a carbon chain by itself or as part of another group of up to 16 carbons, preferably 2 to 10 carbons, containing one double bond such as propenyl, 2-butenyl, 3-butenyl, 2-pentenyl, 4-pentenyl and the like, and may include a halogen substituent such as I, Cl, or F.

The term "alkynyl" by itself or as part of another group as employed herein includes a carbon chain of up to 16 carbons, preferably 2 to 10 carbons, containing one triple bond such as 2-propynyl, 2-butynyl, 3-butynyl and the like.

The term "haloalkyl" as employed herein refers to any of the above alkyl groups substituted by one or more fluorine, chlorine, bromine or iodine atoms, e.g., fluoromethyl, difluoromethyl, trifluoromethyl and chloromethyl.

The term "aminoalkyl" as employed herein refers to any of the above alkyl groups substituted by —NH$_2$.

The term "hydroxyalkyl" as employed herein refers to any of the above alkyl groups substituted by one or more hydroxyl moieties.

The term "BOP" as employed herein refers to benzotriazol-1-yloxytris(dimethylamino)phosphonium hexafluorophosphate (Castro's reagent).

The term "CBZ" as employed herein refers to the amino-protecting group benzyloxycarbonyl.

The term "Phe" refers to the amino acid phenylalanine.

The term "Pro" refers to the amino acid proline.

The amino acids Phe and Pro are α-amino acids that may be selected from the L-amino acids naturally occurring in proteins or the corresponding enantiomeric D-amino acids. The compounds of the present invention preferably include D-Phe and L-Pro.

The compounds of the present invention may be prepared by the general procedures outlined in Schemes 1 and 2.

Scheme 1

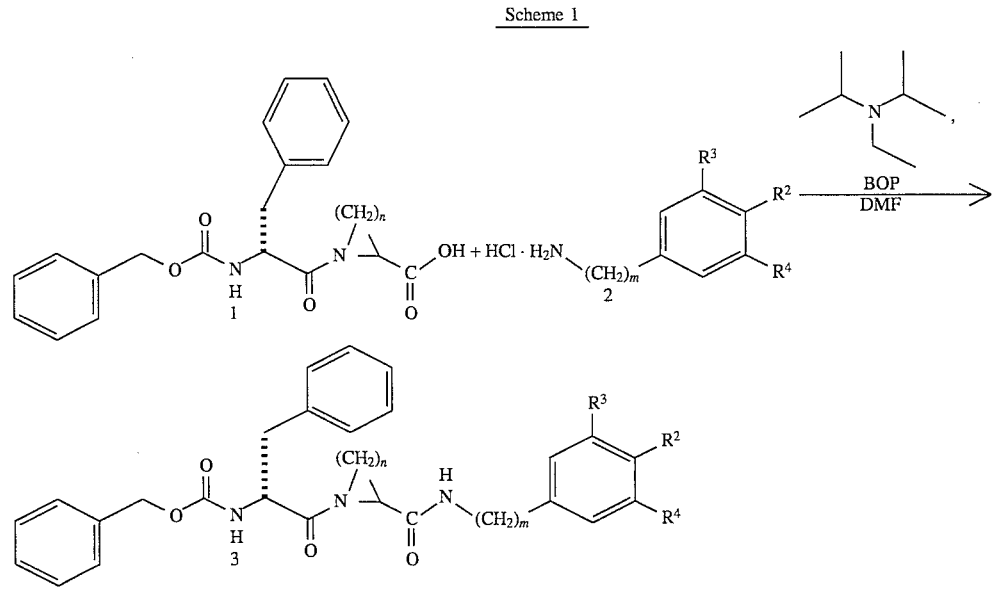

where $R^2$, $R^3$, $R^4$, n and m are as defined above.

The dipeptide starting materials (1) employed to synthesize compounds of the present invention can be obtained using well-known solid phase or solution methods to condense an amino-protected phenylalanine with proline. Other cyclic amino acids, such as azetidinecarboxylic acid and pipecolic acid can be substituted for proline to form compounds of the invention where m is 3 and 5, respectively. These cyclic amino acids are commercially available. Useful amino-protecting groups for forming the starting material (1) include benzyloxycarbonyl (CBZ) or t-butoxycarbonyl (BOC).

Dipeptide (1) is coupled with an appropriate substituted phenylalkylamine (2) using well-known peptide coupling procedures. Reagents for the coupling step include, most preferably, Castro's reagent (BOP)/diisopropylethylamine, or alternatively, hydroxybenzotriazole (HOBT), hydroxysuccinimide, 1,3-dicyclocarbodiimide (DCC), carbonyldiimidazole (CDI), isobutylchloroformate/NEt$_3$, or diphenylphosphorylazide (DPPA)/NEt$_3$. The coupled product is the major product after usual workup.

The amino-protecting group can be removed in a subsequent step as shown in Scheme 2. Thus, compounds where $R^1$ is hydrogen are prepared by hydrogenation of 3. Hydrogenation may be carried out under standard conditions, using for example, a Pd/C catalyst.

Scheme 2

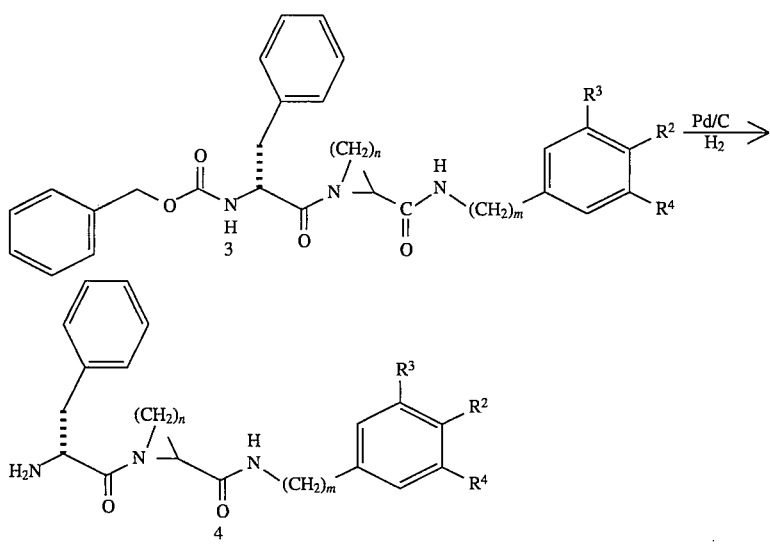

where $R^2$, $R^3$, $R^4$, n and m are as defined above.

Compounds wherein $R^1$ is $-SO_2-R^8$ may be formed by treating a non-protected dipeptide, such as D-Phe-Pro with an appropriate sulfonyl chloride under standard conditions to provide a N-sulfonylated derivative. The N-sulfonylated derivatives may then be employed in place of (1) in Scheme 1.

The compounds of the present invention may be used in combination with thrombolytic agents such as tissue plasminogen activator, streptokinase, and urokinase. Additionally, the compounds of the present invention may be used in combination with other antithrombotic or anticoagulant drugs such as, but not limited to, fibrinogen antagonists and thromboxane receptor antagonists.

The compounds of the present invention may be administered in an effective amount within the dosage range of about 0.1 to about 500 mg/kg, preferably between 0.1 to 10 mg/kg body weight, on a regimen in single or 2–4 divided daily doses.

The pharmaceutical compositions of the invention can be administered to any animal that can experience the beneficial effects of the compounds of the invention. Foremost among such animals are humans, although the invention is not intended to be so limited.

The pharmaceutical compositions of the present invention can be administered by any means that achieve their intended purpose. For example, administration can be by parenteral, subcutaneous, intravenous, intramuscular, intraperitoneal, transdermal, buccal, or ocular routes. Alternatively, or concurrently, administration can be by the oral route. The dosage administered will be dependent upon the age, health, and weight of the recipient, kind of concurrent treatment, if any, frequency of treatment, and the nature of the effect desired.

In addition to the pharmacologically active compounds, the new pharmaceutical preparations can contain suitable pharmaceutically acceptable carriers comprising excipients and auxiliaries that facilitate processing of the active compounds into preparations that can be used pharmaceutically.

The pharmaceutical preparations of the present invention are manufactured in a manner that is, itself, known, for example, by means of conventional mixing, granulating, drageemaking, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. Dragee cores are provided with suitable coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethylcellulose phthalate, are used. Dye stuffs or pigments can be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer, such as, glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids, such as, fatty oils or liquid paraffin. In addition, stabilizers may be added.

Suitable formulations for parenteral administration include aqueous solutions of the active compounds in water-soluble form, for example, water-soluble salts and alkaline solutions. Especially preferred alkaline salts are ammonium salts prepared, for example, with Tris, choline hydroxide, Bis-Tris propane, N-methylglucamine, or arginine. In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example, sodium carboxymethyl cellulose, sorbitol, and/or dextran. Optionally, the suspension may also contain stabilizers.

The following examples are illustrative, but not limiting, of the method and compositions of the present invention. Other suitable modifications and adaptations of the variety of conditions and parameters normally encountered and obvious to those skilled in the art are within the spirit and scope of the invention.

Example 1

Preparation of N-CBZ-D-phenylalanyl-N-[2-(4-hydroxy-3-methoxybenzyl)]-L-prolinamide (6)

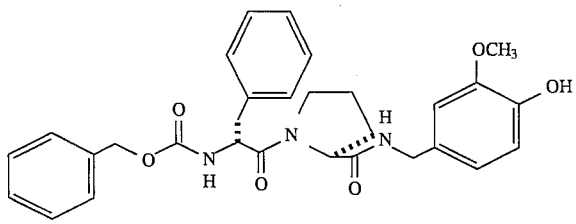

A solution of N-carboxybenzoyl-D-phenylalanine-proline (N-CBZ-D-Phe-Pro) (5) (0.20 g, 0.5 mmol), benzotriazole-1-yloxytris (dimethylaminophosphonium hexafluorophosphate (Castro's Reagent) (0.23 g, 0.52 mmol), and diisopropylethylamine (0.5 mL, 2.87 mmol) in DMF (1.5 mL) was treated with 4-hydroxy-3-methoxybenzylamine•HCl (0.098 g, 0.51 mmol) at room temperature for 1 h. The reaction mixture was quenched with saturated NaHCO$_3$ (5 mL) and extracted with ethyl acetate (15 mL). The organic layer was washed with saturated NaHCO$_3$ (2×5 mL), dried over anhydrous MgSO$_4$, and evaporated to dryness. The residue was purified by silica gel chromatography (10 g) using ethyl acetate as the eluting solvent to give 0.216 g (82% yield) of solid after evaporation. $^1$H-NMR (CDCl$_3$; 300 MHz) δ2.19–2.26 (m, 2H), 2.56 (q, 2H), 3.62 (t, 2H), 3.87 (s, 3H), 4.17 (dd, 1H, J=15.5 Hz), 4.83 (d, 1H, J=12 Hz), 5.35 (d, 1H, J=6.2 Hz), 5.53 (1H), 6.71 (s, 1H), 6.79 (s, 1H), 6.81 (d, 1H), 7.19–7.36 (m, 10H).

Example 2

Preparation of D-phenylalanyl-N-[2-(4-hydroxy-3-methoxybenzyl)]-L-prolinamide (7)

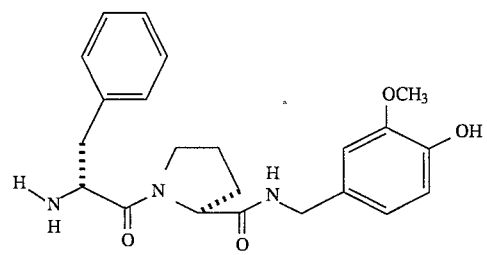

A solution of N-CBZ-D-phenylalanyl-N-[2-(4-hydroxy-3-methoxybenzyl)]-L-prolinamide (6) (0.162 g, 0.3 mmol) in 4:1 ethanol/THF (5 mL) was treated with 10% palladium on carbon (40 mg) and stirred at room temperature under hydrogen atmosphere for 5 h. The reaction mixture was filtered through a Celite (Celite is a registered trademark of the Johns-Manville Product Corporation for diatomaceous earth) pad and washed with methanol. The combined filtrate was evaporated and dried under high vacuum to give a white solid (0.122 g, 100% yield). $^1$H-NMR (CDCl$_3$; 300 MHz) δ3.42–3.49 (m, 2H), 3.73–3.8 (m, 2H), 4.25 (dd, 1H), 4.40 (dd, 1H), 4.47 (dd, 1H), 6.74 (dd, 1H, J=1.8,8 Hz), 6.80 (d, 1H, J=1.8 Hz), 6.83 (d, 1H), 7.0–7.3 (m, 5H). Mass spectrum (MALDI-TOF, m/z): Calcd. for $C_{22}H_{27}N_3O_4$, 402.2 (M+Na$^+$). Found: 419.9.

Example 3

Preparation of N-CBZ-D-phenylalanyl-N-[2-(4-dimethylaminobenzyl)]-L-prolinamide (8)

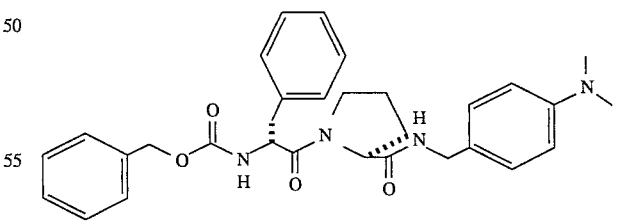

The title compound (265 mg) was prepared using the same procedure as in Example 1 employing 4-(dimethylamino)benzylamine•2 HCl (115 mg) as the coupling amine: $^1$H-NMR (CDCl$_3$; 300 MHz) δ2.56 (q, 1H), 2.84 (s, 6H), 3.60 (t, 1H), 4.21 (dd, 1H), 4.38 (dd, 1H), 4.51 (q, 2H), 4.63 (d, 1H), 4.89 (d, 1H), 5.39 (d, 1H, J=6 Hz), 6.7 (d, 2H), 7.1 (d, 2H), and 7.2–7.4 (m, 9H).

Example 4

Preparation of D-phenylalanyl-N-[2-(4-dimethylaminobenzyl)]-L-prolinamide (9)

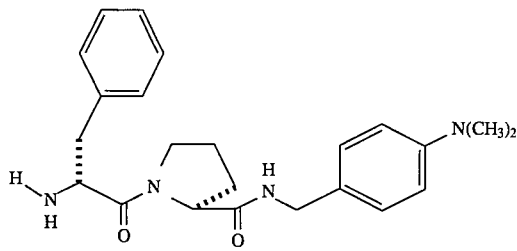

The title compound was obtained (40 mg) from the corresponding CBZ derivative (8) (207 mg) using the procedure outlined in Example 2: $^1$H-NMR (CDCl$_3$; 300 MHz) δ2.92 (s, 6H), 3.45 (dt, J =3, 9 Hz), 3.74 (dd, 1H), J =7, 8 Hz), 4.22 (dd, 1H, J=6, 14 Hz), 4.36 (dd, 1H, J=6, 14 Hz), 4.49 (d, 1H, 2 Hz), 6.67 (d, 2H, J=9 Hz), 7.02–7.32 (m, 7H). Mass Spectrum (MALDI-TOF) calcd. for C$_{23}$H$_{30}$N$_4$O$_2$: 417.2 (M+Na). Found: 416.8.

Example 5

Preparation of N-CBZ-D-phenylalanyl-N-[2-(3,4-dihydroxyphenethyl)]-L-prolinamide (10)

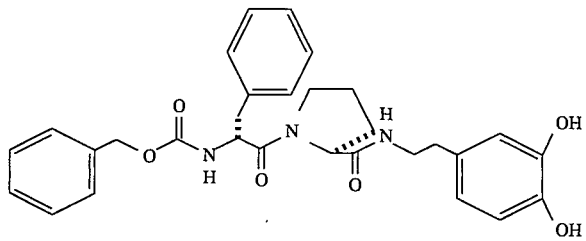

The title compound was prepared using the same procedure as in Example 1 employing 3,4-dihydroxyphenethylamine•HCl as the coupling amine: $^1$H NMR (CDCl$_3$; 300 MHz) δ1.43–1.57 (m, 3H), 2.02–2.17 (m, 1H), 2.47–2.56 (m, 2H), 2.65–2.71 (m, 1H), 2.88–3.02 (m, 2H) 3.06–3.19 (m, 1H), 3.43–3.56 (m, 2H), 4.44–4.52 (m, 2H) 4.65 (d, 1H, J=12.2 Hz), 4.91 (d, 1H, J=12.2 Hz), 5.81 (d, 1H, J=5.4 Hz), 6.5 (d, 1H, J=7.6 Hz), 6.70 (s, 1H), 6.72 (d, 1H, J=7.8 Hz), 7.00 (s, 1H), 7.17–7.28 (m, 10H). Mass Spectrum (MALDI-TOF) calcd. for C$_{30}$H$_{33}$N$_3$O$_6$: 554.6 (M+Na). Found: 554.1.

Example 6

Preparation of N-CBZ-D-phenylalanyl-N-[2-(4-hydroxyphenethyl)]-L-prolinamide (11)

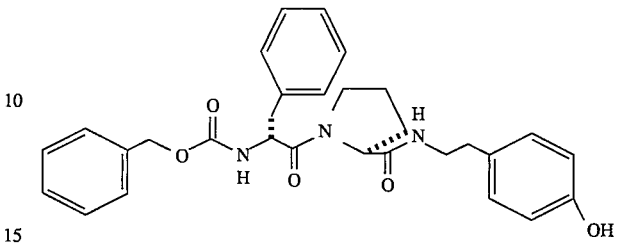

The title compound was prepared using the same procedure as in Example 1 employing 4-hydroxyphenethylamine as the coupling amine: $^1$H NMR (CDCl$_3$; 300 MHz) δ1.43–1.56 (m, 3H), 2.42–2.50 (m, 1H), 2.61–2.70 (m, 2H), 2.93–3.04 (m, 2H), 3.22–3.30 (m, 1H), 3.37–3.50 (m, 3H), 4.41–4.51 (m, 2H), 5.00 (ABq, 2H, J=12.3 Hz), 5.86 (d, 1H, J=6.2 Hz), 6.72 (d, 2H, J=8.0 Hz), 6.95 (d, 2H, J=8.0 Hz), 6.96–7.00 (m, 1H), 7.02–7.33 (m, 10H). Mass Spectrum (MALDI-TOF) calcd. for C$_{30}$H$_{33}$N$_3$O$_5$: 538.6 (M +Na). Found: 539.4.

Example 7

Preparation of N-CBZ-D-phenylalanyl-N-[2-(4-aminobenzyl)]-L-prolinamide (12)

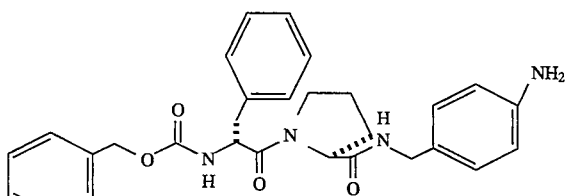

A solution of N-CBZ-D-Phe-Pro (5) (0.793 g, 2.0 mmol), 4-aminobenzylamine (0.366 g, 3.0 mmol), diphenylphosphoryl azide (0.55 g, 2.0 mmol), and triethylamine (0.3 g, 3.0 mmol) in DMF (2 mL) was stirred at 0° C. for 2 h and at room temperature for 3 h. Ethyl acetate (150 mL) was added and the organic layer was washed with saturated NaHCO$_3$ (2×50 mL) and water (2×50 mL). The ethyl acetate was dried over anhydrous Na$_2$SO$_4$ and evaporated to dryness. The residue was purified by flash silica gel chromatography using ethyl acetate as the eluting solvent to give 0.92 g (92% yield) of white foam after evaporation. $^1$H-NMR (CDCl$_3$; 300 MHz) δ1.70 (m, 4H), 2.25 (d, 1H), 2.55 (q, 1H), 2.98 (d, 2H), 3.49 (s, 2H), 3.60 (t, 1H), 4.30 (m, 2H), 4.50 (d, 2H), 4.72 (d, 1H), 4.90 (d, 1H), 5.43 (d, 1H), 6.58 (d, 2H), 6.99 (d, 2H), 7.26 (m, 10H). Mass spectrum (MALDI-TOF, sinapinic acid, m/z): Calcd. for C$_{29}$H$_{32}$N$_4$O$_4$, 523.6 (M+Na$^+$). Found: 523.6.

Example 8

Preparation of D-phenylalanyl-N-[2-(4-aminobenzyl)]-L-prolinamide (13)

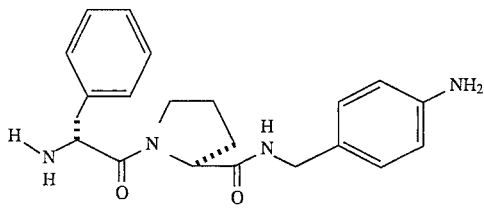

A solution of N-CBZ-D-phenylalanyl-N-[2-(4-aminobenzyl)]-L-prolinamide (12) (0.5 g, 1.0 mmol) in ethanol (15 mL) was treated with 10% palladium on carbon (50 mg) and stirred at room temperature under hydrogen atmosphere (balloon) for 2 h. The reaction mixture was filtered through Celite and was washed with methanol. The combined filtrate was evaporated and dried under high vacuum to give a white solid (0.32 g, 90% yield). $^1$H-NMR (CD$_3$OD; 300 MHz) δ1.84 (m, 4H), 2.87 (t, 2H), 3.34 (d, 2H), 3.44 (m, 1H), 3.83 (m, 1H), 4.23 (d, 2H), 6.69 (d, 2H), 7.00 (d, 2H), 7.25 (m, 5H). Mass spectrum (MALDI-TOF, sinapinic acid, m/z): Calcd. for C$_{21}$H$_{26}$N$_4$O$_2$, 389.4 (M+Na$^+$). Found: 389.6.

Example 9

Preparation of N-CBZ-D-phenylalanyl-N-[2-(4-aminophenethyl)]-L-prolinamide (14)

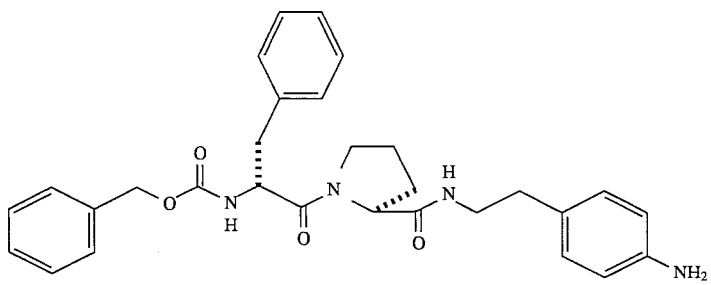

The title compound was prepared using the same procedure as in Example 7 employing 4-aminophenethylamine as the coupling amine: $^1$H-NMR (CDCl$_3$; 300 MHz) δ1.28–1.51 (m, 2H), 2.15–2.21 (m, 1H), 2.47–2.55 (m, 1H), 2.57–2.73 (m, 2H), 2.88–3.00 (m, 2H), 3.23–3.28 (m, 1H), 3.30–3.51 (m, 3H), 4.41 (d, 1H, J=7 Hz), 4.52 (dd, 1H, J=7 and 15 Hz), 5.08 (ABq, 2H, J=12.3 Hz), 5.45 (d, 1H, J=7 Hz), 6.58 (d, 2H, J=8 Hz), 6.90–6.92 (m, 1H), 6.94 (d, 2H, J=8.3 Hz), 7.18–7.39 (m, 10H). Mass Spectrum (MALDI-TOF) calcd. for C$_{30}$H$_{34}$N$_4$O$_4$: 537.5 (M+Na). Found: 537.2.

Example 10

Preparation of N-CBZ-D-phenylalanyl-N-[2-(3,5-dimethoxy-4hydroxyphenethyl)]-L-prolinamide (15)

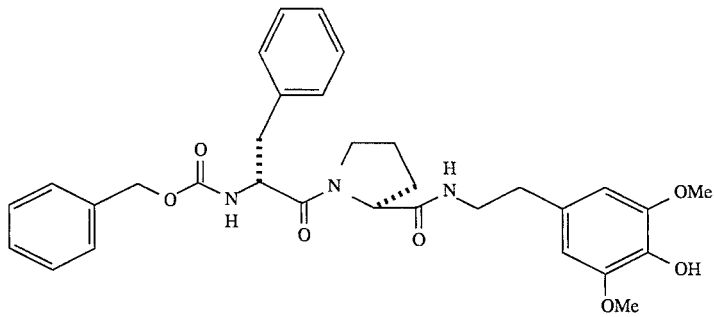

To a solution of N-CBZ-D-Phe-Pro (5) (250 mg, 0.631 mmol), 3,5-dimethoxy-4-hydroxyphenethylamine hydrochloride (162 mg, 0.694 mmol) and N,N-diisopropylethylamine (0.329 mL, 1.89 mmol) in 1.0 mL of DMF was added diphenylphosphoryl azide (0.139 mL, 0.644 mmol) and the mixture stirred at ambient temperature. After 1.5 h, an additional 0.020 mL of diphenylphosphoryl azide was added. After stirring an additional 1 h, the reaction mixture was partitioned between 35 mL of 1,1,1-trichloroethane and 35 mL of 1N HCl. The aqueous layer was extracted with 25 mL of ethyl acetate and the combined organic phases evaporated to a white semisolid. Redissolved in 40 mL ethyl acetate and washed with water (2×25 mL), 1M HCl (2×25 mL) and brine. Dried solution over $Na_2SO_4$ and concentrated in vacuo to a white solid. Recrystallization from ether afforded 334 mg (92%) of a crystalline solid: $^1$H-NMR ($CDCl_3$; 300 MHz) δ1.50–1.74 (m, 3H), 2.16 (m, 1H), 2.54 (m, 1H), 2.70 (m, 1H), 2.99 (m, 1H), 3.28–3.53 (m, 3H), 3.82 (s, 3H), 4.43 (d, 1H, J=6.0 Hz), 4.50 (dd, 2H), 5.07 (dd, 2H), 5.40 (br s, 3H), 5.47 (d, 1H, J=6.5 Hz), 6.42 (s, 2H), 6.96 (br t, 1H) and 7.18–7.38 (m, 10H). Mass spectrum (MALDI-TOF) calcd. for $C_{31}H_{35}N_3O_6$: 598.3 (M +Na). Found: 598.1.

Example 11

Preparation of N-CBZ-D-phenylalanyl-N-[2-(3-methoxy-4-hydroxyphenethyl)]-L-prolinamide (16)

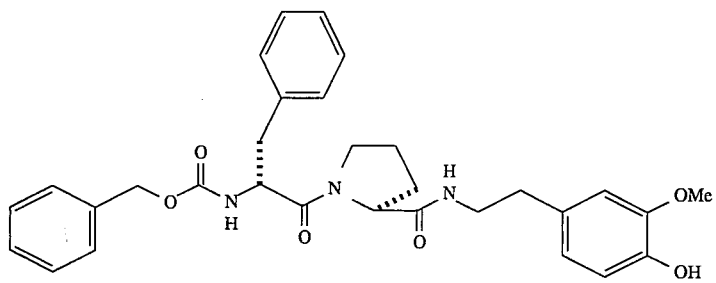

To a solution of N-CBZ-D-Phe-Pro (5) (250 mg, 0.631 mmol), 4-hydroxy-3-methoxyphenethylamine hydrochloride (141 mg, 0.694 mmol) and N,N-diisopropylethylamine (0.329 mL, 1.89 mmol) in 1.0 mL of DMF was added diphenylphosphoryl azide (0.139 mL, 0.644 mmol) and the mixture stirred at ambient temperature. After 1.5 h, an additional 0.020 mL of diphenylphosphoryl azide was added. After stirring an additional 1 h, the reaction mixture was partitioned between 35 mL of 1,1,1-trichloroethane and 35 mL of 1N HCl. The aqueous layer was extracted with 25 mL of ethyl acetate and the combined organic phases evaporated to a white solid. Recrystallization from methanol-ether afforded 341 mg (99%) of the title product as a white powder: $^1$H-NMR (DMSO-$d_6$; 300 MHz) (complex rotamer mixture) δ1.53–1.78 (m, 2H), 1.88 and 2.16 (rotamers, m, 1H), 2.53–2.68 (m, 2H), 2.70–2.97 (m, 2H), 3.08–3.18 (m, 1H), 3.20–3.29 (m, 1H), 3.53 and 4.08 (rotamers, m, 1H), 3.71 (s, 3H), 4.17 (t, 1H), 4.94 and 5.01 (rotamers, overlapping dd, 2H), 6.56 (td, 1H, J=7.9, 1.6 Hz), 6.67 (d, 1H, J=8.0 Hz), 6.72 (br s, 1H), 7.18–7.35 (m, 10H), 7.47 and 8.34 (rotamers, br t, 1H, J=5.5 Hz), 7.83 and 7.88 (rotamers, d, 1H,) 8.78 (d, 1H, J=10.5 Hz). Mass spectrum (MALDI-TOF) calcd. for $C_{31}H_{35}N_3O_6$: 568.2 (M+Na). Found: 568.1.

Example 12

In Vitro Inhibition of Purified Enzymes

The ability of the compounds of the present invention to act as inhibitors of thrombin, factor Xa and plasmin catalytic activity was assessed by determining the concentration which inhibited enzyme activity by 50% using purified human enzymes. The concentration of added inhibitor that caused a 50% decrease in the initial rate of hydrolysis was defined as the $IC_{50}$ value.

All assays are based on the ability of the test compound to inhibit the hydrolysis of a peptide p-nitroanilide substrate. In a typical experiment, appropriate substrate is prepared in DMSO, and diluted into an assay buffer consisting of 50ram HEPES and 130 mM NaCl at a pH of 7.5. The final concentration for each of the substrates is listed below. All substrate concentrations are at least 10 fold lower than $K_m$ to insure inhibition is competitive. Test compounds are prepared as 1 mg/ml solutions in DMSO, and three additional 10-fold dilutions in DMSO are prepared. Enzyme solutions are prepared at the concentrations listed below in assay buffer.

In a typical $IC_{50}$ determination, into each well of a 96 well plate is pipetted 280 uL of substrate solution, 10 μL of inhibitor solution, and the plate is allowed to thermally equilibrate at 37° C. in a Molecular Devices Plate Reader for at least 10 minutes. Reactions are initiated by the addition of a 20 μL aliquot of enzyme, and the absorbance increase at 405 nm is recorded for 15 minutes. Data corresponding to less than 10% of the total substrate hydrolysis is used in the calculations. The ratio of the velocity (rate of the change in absorbance as a function of time) for a sample containing no inhibitor is divided by the velocity of a sample containing inhibitor, and is plotted as a function of inhibitor concentration. The inverse of the slope is the concentration of inhibitor which produces a 50% decrease in activity of the enzyme. This concentration is referred to as the $IC_{50}$.

Thrombin

Thrombin activity was assessed as the ability to hydrolyse the substrate N-benzoyl-Phe-Val-Arg-p-nitroanilide (Bz-Phe-Val-Arg-pNa), and was obtained from Sigma Chemical Company (St. Louis, Mo.). Substrate solutions were prepared at a concentration of 60 μM (60 μM<<$K_m$=1.2 mM) in assay buffer. Final DMSO concentration was 0.3%. Purified human α-thrombin was obtained from Enzyme Research Laboratories, Inc., and was diluted into assay buffer to a concentration of 1.2 μM. Final reagent concentrations were: [thrombin]=36 nM, [Bz-Phe-Val-Arg-pNa]=66 μM, [inhibitor]=60 to 0.06 μM.

Factor Xa

Factor Xa activity was assessed as the ability to hydrolyse the substrate Bz-Ile-Glu-Gly-Arg-pNa, and was obtained from Sigma. Substrate solutions were prepared at a concentration of 26 μM (26 μM<<$K_m$=1.3 mM) in assay buffer. Final DMSO concentration was 0.3%. Activated factor Xa was obtained from Enzyme Research Laboratories, Inc., and was diluted into assay buffer to a concentration of 1.2 μM. Final reagent concentrations were: [Factor Xa]=10 nM, [Bz-Ile-Glu-Gly-Arg-pNa]=26 μM, [inhibitor]=60 to 0.06 μM.

Plasmin

Plasmin activity was assessed as the ability to hydrolyse the substrate Tos-Gly-Pro-Lys-pNa, and was obtained from Sigma. Substrate solutions were prepared at a concentration of 22 μM (22 μM<<$K_m$=240 μM) in assay buffer. Final DMSO concentration was 0.3%. Purified human plasmin was obtained from Enzyme Research Laboratories Inc, and was diluted into assay buffer to a concentration of 1.2 μM. Final reagent concentrations were: [plasmin]=15 nM, [Bz-Ile-Glu-Gly-Arg-pNa]=26 μM, [inhibitor]=60 to 0.06 μM.

The results obtained employing the compounds 13, 7 and 12, respectively, are given in Table 1.

TABLE 1

| Compound Structure | Thrombin Inhibition $IC_{50}$ (μM) | Factor Xa % Inhibition at 60 μM | Plasmin % Inhibition at 60 μM |
|---|---|---|---|
| (13) | 1 | 0% | — |
| (7) | 4.7 | 0% | 0% |
| (12) | 2.8 | — | — |

The results indicate that the compounds of the present invention, and specifically the compounds of Examples 2, 7 and 8 are highly selective and potent inhibitors of thrombin.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:
1. A compound having the Formula I:

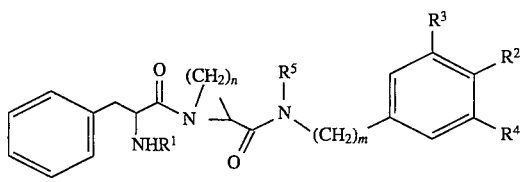

or a pharmaceutically acceptable salt thereof;
wherein $R^1$ is one of hydrogen, $SO_2R^8$, —$CONHR^8$ $CO_2R^8$, where $R^8$ is one of hydrogen, $C_1$–$C_8$ alkyl, $C_2$–$C_{10}$ alkenyl, $C_2$–$C_{10}$ alkynyl, $C_6$–$C_{10}$ aryl or $C_6$–$C_{10}$ aryl $C_1$–$C_6$ alkyl;

$R^2$ is one of hydroxy or —$NR^6R^7$;

$R^3$ and $R^4$ are independently one of hydrogen, hydroxy, —$NR^6R^7$, $C_1$–$C_8$ alkyl, $C_6$–$C_{10}$ aryl, $C_6$–$C_{10}$ aryl $C_1$–$C_6$ alkyl, $C_1$–$C_8$ alkoxy, halogen, $C_1$–$C_8$ haloalkyl, $C_1$–$C_8$ aminoalkyl or $C_1$–$C_8$ hydroxyalkyl;

$R^5$, $R^6$ and $R^7$ are independently one of hydrogen, $C_1$–$C_8$ alkyl, $C_6$–$C_{10}$ aryl or $C_6$–$C_{10}$ aryl $C_1$–$C_6$ alkyl;

n is 3; and m is from 1 to 6;

provided that when $R^2$ is —$NR^6R^7$, then one or both of $R^3$ and $R^4$ is other than hydrogen, fluoro or $C_1$–$C_8$ alkyl.

2. A pharmaceutical composition comprising an effective amount of a compound of claim 1 and a pharmaceutically acceptable carrier or diluent.

3. The compound of claim 1, wherein $R^1$ is one of hydrogen or —$CO_2$-benzyl;

$R^2$ is hydroxy;

$R^3$ and $R^4$ are each independently one of hydrogen, hydroxy or methoxy;

$R^5$ is hydrogen; and m is 1 or 2.

4. A compound having the Formula I:

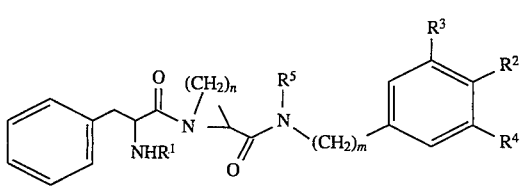

or a pharmaceutically acceptable salt thereof;
wherein $R^1$ is one of hydrogen, —$CO_2R^8$, where $R^8$ is one of $C_1$–$C_8$ alkyl, $C_6$–$C_{10}$ aryl or $C_6$–$C_{10}$ aryl $C_1$–$C_6$ alkyl;

$R^2$ is hydroxy;

$R^3$ and $R^4$ are independently one of hydrogen, hydroxy, $C_1$–$C_6$ alkyl or $C_1$–$C_6$ alkoxy;

$R^5$, $R^6$ and $R^7$ are independently one of hydrogen, $C_1$–$C_8$ alkyl, $C_6$–$C_{10}$ aryl or $C_6$–$C_{10}$ aryl $C_1$–$C_6$ alkyl;

n is 3; and m is from 1 to 6.

5. The compound of claim 1, which is one of: N-benzyloxycarbonyl-D-phenylalanyl-N-{2-(4-hydroxy-3-methoxybenzyl)}-L-prolinamide, D-phenylalanyl-N-{2-(4-hydroxy-3-methoxybenzyl)}-L-prolinamide, N-benzyloxycarbonyl-D-phenylalanyl-N-{2-(3,4-dihydroxyphenethyl)}-L-prolinamide, N-benzyloxycarbonyl-D-phenylalanyl-N-{2-(4-hydroxyphenethyl)}-L-prolinamide, N-benzyloxycarbonyl-D-phenylalanyl-N-{2-(3,5-dimethoxy-4-hydroxyphenethyl)}-L-prolinamide, and N-benzyloxycarbonyl-D-phenylalanyl-N-{2-(3-methoxy-4-hydroxyphenethyl)}-L-prolinamide.

6. A method of treating thrombosis, ischemia, stroke, restenosis or inflammation comprising administering to a mammal in need of said treatment a therapeutically or prophylactically effective amount of a compound of claim 4.

7. A method of treating thrombosis, ischemia, stroke, restenosis or inflammation comprising administering to a mammal in need of said treatment a therapeutically or prophylactically effective amount of a compound of claim 3.

8. The compound of claim 4, wherein $R^1$ is hydrogen.

9. The compound of claim 4, wherein $R^1$ is —$CO_2$—$R^8$, and $R^8$ is benzyl.

10. The compound of claim 4, wherein $R^6$ and $R^7$ are independently one of hydrogen or $C_{1-6}$alkyl.

11. The compound of claim 5 which is D-phenylalanyl-N-[2-(4-hydroxy-3-methoxybenzyl)]-L-prolinamide.

12. A method of treating thrombosis, ischemia, stroke, restenosis or inflammation comprising administering to a mammal in need of said treatment a therapeutically or prophylactically effective amount of a compound of claim 1.

13. A method of treating thrombosis, ischemia, stroke, restenosis or inflammation comprising administering to a mammal in need of said treatment a therapeutically or prophylactically effective amount of one of the compounds of claim 5.

14. The compound of claim 4, wherein m is 1 or 2.

* * * * *